United States Patent [19]

Grier

[11] 4,011,236

[45] Mar. 8, 1977

[54] N-(BENZIMIDAZOL-2-YL)ARYLCARBOXA-MIDES AS ULTRAVIOLET (UV) LIGHT ABSORBERS

[75] Inventor: Nathaniel Grier, Englewood, N.J.

[73] Assignee: Merck & Co., Inc., Rahway, N.J.

[22] Filed: May 27, 1975

[21] Appl. No.: 580,847

Related U.S. Application Data

[60] Division of Ser. No. 320,231, Jan. 2, 1973, Pat. No. 3,907,700, which is a continuation-in-part of Ser. No. 758,601, Sept. 9, 1968, abandoned.

[52] U.S. Cl. .................. 260/309.2; 260/243 A; 260/244 R; 260/250 R; 260/250 A; 260/256.4 R; 260/279 R; 260/287 R; 260/295 K; 260/295.5 B; 260/306.8 R; 260/307 R; 260/240 R; 260/240 J

[51] Int. Cl.² ........................... C07D 235/30

[58] Field of Search ..................... 260/309.2

[56] References Cited

UNITED STATES PATENTS

| | | | |
|---|---|---|---|
| 3,095,422 | 6/1963 | Duennenberger et al. | 260/309.2 |
| 3,255,202 | 6/1966 | Johnson | 260/309.2 |
| 3,401,171 | 9/1968 | Craig et al. | 260/309.2 |
| 3,401,173 | 9/1968 | Chow et al. | 260/309.2 |

OTHER PUBLICATIONS

Grier Chem. Abst. 1970, Vol. 72, No. 132730j.

*Primary Examiner*—Natalie Trousof
*Attorney, Agent, or Firm*—Edmunde D. Riedl; Julian S. Levitt

[57] ABSTRACT

This invention relates to compositions containing N-(benzimidazol-2-yl)arylcarboxamides as ultraviolet (UV) light absorbers. The compounds are useful to protect UV sensitive materials, particularly plastic compositions, or ingredients thereof such as dyes, antimicrobial agents, or plasticizers from attack by ultraviolet light. The compositions are suitable for those uses where UV protection is required only for short periods of time, for example in sun tan lotions, as well as for uses which require protection for extended periods of time.

1 Claim, No Drawings

N-(BENZIMIDAZOL-2-YL)ARYLCARBOXAMIDES AS ULTRAVIOLET (UV) LIGHT ABSORBERS

This application is a division of U.S. Ser. No. 320,231, filed Jan. 2, 1973, now U.S. Pat. No. 3,907,700 which is a continuation-in-part of prior copending application Ser. No. 758,601, filed Sept. 9, 1968 now abandoned.

This invention relates to compositions containing selective light arresters which exhibit high absorption capacities for incident ultraviolet radiation. More particularly this invention relates to compositions containing N-(benzimidazol-2-yl)aryl or (heteroaryl)-carboxamides as ultraviolet absorbers.

Ultraviolet radiation can interact with a variety of materials to produce deleterious effects. Fortunately, a good proportion of this energy originating from the sun is removed by the earth's atmosphere. In the ultraviolet region, which comprises about 5% of the total incident solar energy, the energy content decreases in intensity from 400 millimicrons to practically zero at 290 millimicrons. However, the lower wave length region of this energy segment is a primary factor in the rapid destruction of many substances including plastics, wood, textiles, leather, coatings, etc. For the protection of these materials against degradation certain ultraviolet light-absorbing compounds, commonly called U.V. absorbers, and characterized by having peak absorption in the range of from about 300 – 350 millimicrons are frequently employed.

It has been discovered that benzimidazoles substituted in the 2-position by an aroylamino or heteroaroylamino group are capable of being highly efficient absorbers of UV energy in the region of 300–350 m$\mu$, along with an inherent ability to dissipate harmlessly the acquired energy without affecting the exposed system or components contained therein, and without self destruction.

The N-(benzimidazol-2-yl)arylcarboxamide or N-(benzimidazol-2-yl)heteroarylcarboxamide compounds which find novel use in this invention may be represented structurally by the formula I below

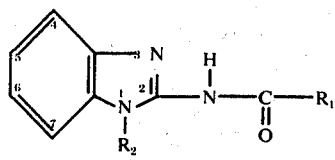

In this formula $R_1$ represents an aromatic radical having 1–3 nuclei, including a carbocyclic aryl radical such as phenyl, biphenyl, naphthyl, anthryl, phenanthryl, and the like, and a heterocyclic aryl radical such as furan, thiophene, pyridine, pyridazine, pyrimidine, pyrazine, quinoline, isoquinoline, acridine, phenanthridine, phenazine, phenoxazine, phenthiazine, coumarone, benzothiophene, indole, pyrazole, imidazole, thiazole, oxazole, triazole, carbazole and the like. Specifically excluded from the invention are aliphatic acid amides of 2-aminobenzimidazole (where $R_1$ is alkyl); they fail to protect against UV. In addition $R_1$ can be a phenyl group substituted at the 2-, 3- or 4-position by a member selected from the group consisting of methoxycarbonyl, ethoxycarbonyl, butoxycarbonyl, propoxycarboxyl, dodecyloxycarbonyl, carboxy, phenyl, nitro, and carboxamido and $R_2$ is a member selected from the group consisting of hydrogen, methyl, acetyl, methoxycarbonyl, butyryl, pivaloyl, stearoyl, acryl, toluyl, mesitoyl, butyl, octyl, benzoyl, halobenzoyl, and phenyl.

In addition $R_1$ may be attached to the carbonyl through a vinyl group-(CH=CH$_2$). Representative compounds of this type are N-(benzimidazol-2-yl)cinnamamide and 2-(2-furanacrylyl)aminobenzimidazole. These compounds will prevent the development of additional color in sensitive plastics when exposed to UV-light without imparting significant color to the plastic initially. This useful result is accomplished because the cinnamamide compounds are so highly efficient that relatively low concentrations of less than 0.5% by weight need to be employed.

$R_2$ represents hydrogen, alkanoyl, alkenyl, benzoyl, halobenzoyl, alkoxybenzoyl, alkoxycarbonyl, benzoyl, alkyl, phenyl, or aralkyl.

The light absorbing compound may also be a N-(benzimidazol-2-yl)phthalimide, or a phthalamide such as N,N'-bis(benzimidazol-2-yl)phthalamide, N,N'-bis(-benzimidazol-2-yl)isophthalamide, or N,N'-bis(benzimidazol-2-yl)terephthalamide, where two carboxy groups of a benzene polycarboxylic acid from amides with the 2-amino group of the 2-aminobenzimidazole, as is more fully described on page 18a.

The benzene and/or heterocyclic rings present in any of the above described compounds, including the benzene ring of the benzimidazole, a carbocyclic or heterocyclic aryl ring present at $R_1$, and the benzene ring of any phthalimide or phthalamide compound, may be unsubstituted, or substituted by one or more of the following groups: alkyl, which may be straight or branched chain, alkenyl, aryl especially phenyl, phenalkyl or naphthyl, heteroaryl, halogen, nitro, hydroxy, alkoxy, phenoxy or naphthoxy, amino, alkylamino, dialkylamino, phenylamino, phenalkylamino, sulfo, carboxy, alkoxycarbonyl, alkanoyl or benzoyl.

Among the compounds which can be utilized are: N-(5-dodecyloxybenzimidazol-2yl)-2-carboxamidonaphthalene; N-(4-phenylbenzimidazol-2-yl)-4-phenylbenzamide; N-(1-methyl-4-phenylbenzimidazol-2-yl)-3-toluamide; N-(5-dimethylaminobenzimidazol-2yl)-4-nitrobenzamide; N-(benzimidazol-2-yl)-4-carboxamidoimidazole; N-(4-t-butylbenzimidazol-2-yl)-3-carboxamidothiophene; N-(benzimidazol-2-yl)-3,5-di-tert-butylbenzamide; N-(benzimidazol-2-yl)-4-benzyl-1-carboxamidonaphthalene; N-(5-methoxybenzimidazol-2-yl)-4-toluamide; N-(4-phenoxybenzimidazol-2-yl)-4-carboxamidothiazole; N-(1-acetyl-benzimidazol-2-yl)benzamide; N-(benzimidazol-2-yl)-3-sulfobenzamide; N-(benzimidazol-2yl)-3-carboxybenzamide; N-(benzimidazol-2-yl)-8-carboxamidoquinoline; N-(benzimidazol-2-yl)-3-carboxamidoquinoline; N-(benzimidazol-2-yl)-4-carboxamidopyridine; N-(5,6-dimethylbenzimidazol-2-yl)-3-chlorobenzamide; N-(benzimidazol-2-yl)-4-hydroxyethylbenzamide; N-(benzimidazol-2-yl)-4-acetylbenzamide; N-(4-sulfobenzimidazol-2-yl)-3-chlorobenzamide; N-(5-sulfobenzimidazol-2-yl)-4-phenylbenzamide; N-[5-(1-naphthyl)benzimidazol-2-yl)]-4-chlorobenzamide; N-[4-(3-thienyl)benzimidazol-2-yl]-benzamide N-(5-aminobenzimidazol-2-yl)-o-toluamide; N-[4-(n-propylamino)benzimidazol-2-yl]-3-ethylbenzamide; N-[5-(phenylamino)benzimidazol-2-yl]-4-methoxybenzamide; N-[4-(benzylamino)benzimidazol-2-yl]naphthalene-2-carboxamide; N-(5- nitrobenzimidazol-2-yl)benzamide; N-[4-cyanobenzimidazol-2-yl]-p-nitrobenzamide; N-(5,6-dimethylbenzimidazol-2-yl)-o-tolumaide; N-(5,6-dimethylbenzimidazol-2-yl)-p-toluamide; N-(5-acetamido)benzimidazol-2-benzamide; N-(5-benzamido)benzimidazol-2yl)-benzamide; N-(5-methoxybenzimidazol-2-yl)benzamide; N-(4-lauroyloxy)benzimidazol-2-yl)benzamide; N-(5,6-dimethylbenzimidazol-2-yl)-o-toluamide; N-(5,6-dimethyl-benzimidazol-2-yl)p-toluamide; N-(5-acetamido)benzimidazol-2-yl)benzamide; N-(5-benzamido)benzimidazol-2-yl)benzamide; N-(5-methoxybenzimidazol-2-yl)benzamide; N-(4-lauroyloxy)benzimidazol-2-yl)benzamide; N-(benzimidazol-2-yl)-2-benzoylbenzamide; N-(benzimidazol-2-yl)-4-benzoylbenzamide; N-(5-chloro-1-methoxycarbonylbenzimidazol-2-yl)benzamide; N-[4-(4-chlorophenyl)benzimidazol-2-yl]benzamide; N-5-aminobenzimidazol-2-yl)benzamide; N-(benzimidazol-2-yl)-α-anthranamide; N-(1-n-butyrylbenzimidazol-2-yl)-benzamide; N-(1-pivaloylbenzimidazol-2-yl)benzamide; N-(1-stearoylbenzimidazol-2-yl)benzamide; N-(1-acrylylbenzimidazol-2-yl)benzamide; N-(1-benzoylbenzimidazol-2-yl)-benzamide; N-(1-p-toluylbenzimidazol-2-yl)benzamide; N-(1-mesitoylbenzimidazol-2-yl)benzamide; N-(1-n-butylbenzimidazol-2-yl)benzamide; N-(1-n-octylbenzimidazol-2-yl)benzamide; N-(1-phenylbenzimidazol-2-yl)benzamide; N-(1-methoxycarbonyl-2-yl)benzamide; N-(benzimidazol-2-yl)-4-hydroxybenzamide; N-(5-methylbenzimidazol-2-yl)-2-phenoxybenzamide; N-(5,6-dimethylbenzimidazol-2-yl)-4-amino-2-methylbenzamide; N-(benzimidazol-2-yl)-3-methylaminoisonicotinamide; N-(benzimidazol-2-yl)-3-benzylbenzamide; N-(4-methylbenzimidazol-2-yl)-4-butoxycarbonylamino benzamide; N-(benzimidazol-2-yl)-3-sulfobenzamide; N-(benzimidazol-2-yl)-2-benzoylbenzamide; N-(benzimidazol-2-yl)-4-benzoylbenzamide; N-(5-chloro-1-methoxycarbonylbenzimidazol-2-yl)benzamide; N-[4-(4-chlorophenyl)benzimidazol-2-yl]benzamide; N-(5-aminobenzimidazol-2-yl)benzamide; N-(benzimidazol-2-yl)-α-anthranamide.

It is known that 2-aminobenzimidazoles show no significant absorption above 300 millimicrons and 2-aroyl- or 2-heteroaroyl-substituted benzimidazoles are rapidly degraded by UV light. For example, in a series of conventional tests utilizing plastic films as substrate, 2-benzoylbenzimidazole incorporation in these films caused greater color formation upon exposure to UV light than the untreated control film. Similar observations were noted for other 2-aroyl and heteroaroyl-substituted benzimidazoles. Evidently, the compounds undergo photochemical transformation to produce highly colored end-products. Surprisingly, the interposition of a carbonylamino group between the 2-position of the benzimidazole and the aryl or heteroaryl substituent provides a significant increase in UV sbsorption efficiency over 2-aminobenzimidazole, especially in the region critical to the stabilization of many substrates, and the 2-aroylaminobenzimidazoles withstand successfully such energy absorption.

One hypothesis which may help to explain the ability of the compounds of this invention to dissipate UV energy in the harmless manner centers upon the possibility of formation of a chelate structure, which can arise by enolization of the amide at least transiently. The postulated chelate structure (I)

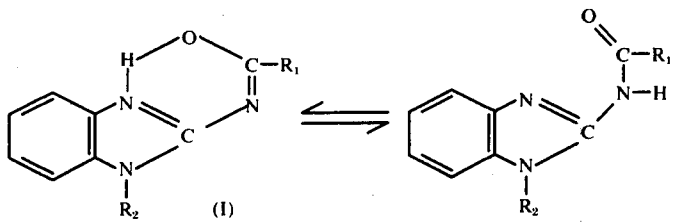

in which $R_1$ is aryl or heteroaryl may provide the resonance path for energy release. However, we do not wish to be bound to such a proposed mechanism. The theory gains support from data showing that a wide variety of substituents can be introduced at $R_1$ and also at the benzo portion (4-, 5-, 6- and 7-position) of the benzimidazole ring system without causing loss of utility and performance.

Table I, listing some 2-aroylaminobenzimidazoles, indicates how particular substituents comprising the acid group of the amide can produce absorption maxima over the useful range and having high efficiencies.

Table I

UV ABSORBERS

| $R_1$ | λ max. (mμ) | $E_{1cm}^{\%*}$ |
|---|---|---|
| 1. CH₃—⟨phenyl⟩— | 301 | 946 |
| 2. CH₃—⟨phenyl⟩— | 301 | 826 |
| 3. (CH₃)₃C—⟨phenyl⟩— | 302 | 737 |
| 4. ⟨phenyl⟩— | 302.5 | 786 |
| 5. ⟨phenyl⟩-⟨phenyl⟩— | 307.5 | 878 |
| 6. F—⟨phenyl⟩— | 307.5 | 775 |
| 7. ⟨phenyl-F⟩— | 308 | 730 |
| 8. ⟨naphthyl⟩— | 312 | 768 |

Table I-continued
UV ABSORBERS

| | $R_1$ | λ max. (mμ) | $E_{1cm}^{1\%}$ |
|---|---|---|---|
| 9. | Cl—⬡— | 313 | 791 |
| 10. | ⬡—CH=CH— | 316 | 1014 |
| 11. | ⬡⟨ (isophthaloyl, di) | 319 | 950 |
| 12. | $C_2H_5OC$—⬡— (with C=O) | 322.5 | 613 |
| 13. | ⬡⟨ (terephthaloyl, di) | 334 | 871 |

$E_{1cm}^{1\%}$ in ethyl alcohol for all compounds except 11 and 13 (in dimethylformamide)

The heteroaroylaminobenzimidazoles are also surprisingly effective, useful screening agents. They, too, absorb energy in the critical range, that is, between 300 and 350 millimicrons with a high order of efficiency comparable to the aroyl derivatives outlined in Table 2. Whereas the parent heterocycle, for example, pyridine or thiazole is unstable to UV-light, especially when joined directly to the 2-carbon of benzimidazole, the carboxamido derivatives, for example, 2-nicotinamidobenzimidazole and 2-(thiazole-4-carboxamido)benzimidazole gave significant protection to sensitive polymer systems from the degradative effects of UV-light energy.

The advantages of such a group of compounds over the prior art become especially important because there is a significant increase in stability to air oxidation by elimination of a orthohydroxy-substituted-phenyl requirement, a greater heat and chemical stability based upon the relatively resistant aroyl- and hetero-aroylamide linkage, and increased compatabilities with a variety of substrate systems.

Another unexpected property found is that, although the compounds of this invention are generally soluble in alkaline solution, the solutions show no absorption of light in the visible region, unlike the 2-hydroxyphenyl-containing products of the prior art. Still another most useful characteristic is the ability to prepare these compounds in completely colorless condition. As amides of 2-aminobenzimidazole, they dissolve in strongly acid media without color formation as well. Precipitation from such media, frequently merely by diluting the solution with water, produces snow-white products.

Another significant advantage of the compounds of this invention lies in their low order of volatility. Evidently the amide linkage in these 2-aminobenzimidazole derivatives imparts relatively high resistance to vaporation by heat. These compounds can be subjected to temperatures well above those which most plastics and other light-sensitive materials are subjected to during processing, that is, from 80° F to 400° F, without volatilization.

In one procedure for preparing the aroylamino and heteroaroylaminobenzimidazoles a 2-aminobenzimidazole is reacted with an acid anhydride or an aromatic or heterocycle aromatic nucleus, the acyl radical of the anhydride becoming the acyl substituent on the amino radical of the benzimidazole. This process may be pictured structurally as follows:

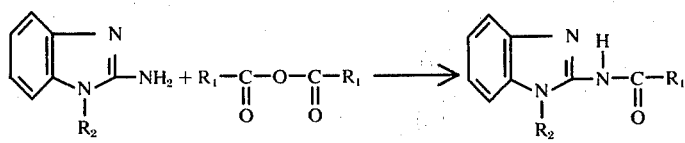

where $R_1$ and $R_2$ are as previously defined. The aromatic rings of the two components of the reaction, that is the anhydride and the 2-aminobenzimidazole can be substituted as defined on page 3. However, additional substituents capable of reacting with anhydrides such as hydroxyl, amino, and mercapto should first be blocked with reagents well known to those skilled in the art before reaction with anhydride. Reactions such as acylation, benzylation, and the like can be employed. After reaction of the 2-aminobenzimidazole with the anhydride, blocking groups can be removed from substituents if desired. In this particular process, essentially equimolar amounts of the two reactants are brought together in a suitable solvent medium. It is preferred to employ a basic solvent such as pyridine, or one of the picolines. For best results, the reaction is brought about at elevated temperatures of about 50°-100° C. for ½-5 hours. The desired 2-acylaminobenzimidazoles may then be recovered by techniques known to those skilled in the art.

Among the compounds which are readily prepared in this manner are: 2-benzamidobenzimidazole, 2-phthalimidobenzimidazole in which the equivalent anhydride structure, that is, the imide is still retained in the end-product, 2-(2-furoylamino)-benzimidazole, N-(5,6-dichlorobenzimidazol-2-yl)benzamide and N-(benzamidazol-2-yl)-4-methoxybenzamide. The 2-phthalimidobenzimidazole serves as a useful intermeidate to prepare 2-benzamidobenzimidazoles in which the benzoyl moiety is substituted in the 2- or 0-position with a carboxyl group. The substituent in this position can be as an ester or an amide, as well as a free carboxyl group. Esters result upon reaction of the phthalimido compound with alcohols or phenols, and amides are the products or reaction with primary and secondary amines.

A second procedure involves the reaction of an arcyl or heteroaroyl halide with 2-aminobenzimidazole, preferably in a basic medium such as pyridine or quinoline. Usually, heating at 100° C for ½-5 hours is sufficient to convert the acyl halide to the corresponding amide. The reaction mixture is generally quenched in water to precipitate the amide. The pyridine HCl reaction product remains soluble in the water.

reaction. This process is illustrated below, where $R_1$ is defined as above:

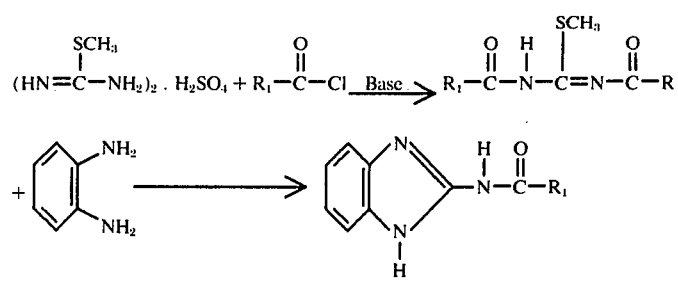

The reaction of an aroyl or heteroaroyl halide with a 2-aminobenzimidazole can also be conducted in chloroform with triethylamine as the HCl acceptor at reflux temperatures for about 2-6 hours. Approximately stoichiometric quantities of reactants are used with an excess of triethylamine. Each of the two components of the reaction can be substituted as defined for $R_1$, $R_2$ as described above for the procedure using the aroyl or heteroaroyl acid anhydride.

Compounds prepared in this way are N-(benzimidazole-2-yl)-4-biphenylcarboxamide; N,N'-bis(benzimidazol-2-yl)-isophthalamide, N,N'-bis(benzimidazol-2-yl)-terephthalamide; 2-(nicotinamido)-benzimidazole; 2-(thiazole-4-carboxamido)benzimidazole, and 2-(β-naphthoyl)amino-benzimidazole.

Compounds having an alkyl or aryl group at the $N_1$-nitrogen of the benzimidazole for example, N-(1-n-butylbenzimidazol-2-yl)benzamide, N-(1-n-octylbenzimidazol-2yl)benzamide, N-(1-phenylbenzimidazol-2-yl)benzamide, are prepared from the 2-aminobenzimidazole which is similarly substituted. The latter compounds are easily prepared by methods known in the art.

Compounds having an aryl group at the $N_1$-nitrogen of the benzimidazole, for example, N-(1-n-butyrylbenzimidazol-2-yl)benzamide, N-(1-pivaloylbenzimidazol-2-yl)benzamide, N-(1-stearoylbenzimidazol-2-yl)benzamide, N-(1-stearoylbenzimidazol-2-yl)benzamide, N-(1-acrylylbenzimidazol-2-yl)benzamide, N-(1-p-toluylbenzimidazol-2-yl)benzamide, N-(1-mesitoylbenzimidazol-2-yl)benzamide, are prepared by reaction of approximately stoichiometric quantities of the 2-carboxamidobenzimidazole and the appropriate acid chloride by gradual addition of the acid chloride to a stirred mixture of the amide in tetrahydrofuran containing an excess of triethylamine. The reaction mixture is maintained at room temperature for 4-8 hours. After removal of the solvent under reduced pressure, the residue is washed with water, filtered and dried.

The 2-aroylamino and 2-heteroaroylaminobenzimidazoles may also be synthesized from 2-methylthiopseudourea (preferably used as sulfate) by reaction of this latter material with an appropriate aroyl or heteroaroyl halide. The reaction requires 2 moles of the acyl halide for every mole of the pseudo-urea compound. It is generally brought about in the presence of an acid binding agent or in an appropriate solvent medium such as dimethylformamide, dimethylacetamide, and the like. The resulting 1,3-diacyl-2-methylthiopseudourea is then reacted with o-phenylenediamine in order to obtain the 2-aroyl or 2-heteroarybylaminobenzmidazole. Any of the acid chlorides used in the previous paragraph are suitable for the where $R_1$ and substituents on the benzene ring of the imidazole are as above defined. Details of this reaction are given in Example 3, where the acid chloride is thenoyl chloride.

Another synthetic process for producing the compounds disclosed herein comprises the reaction of cyanamide with an essentially equimolar amount of an aroyl or heteroaroyl halide in pyridine or other solvent to afford the corresponding acylcyanamide. The resultant acylcyanamide is then reacted with o-phenylenediamine, whereby the desired 2-aroylamino or 2-heteroaroylaminobenzimidazole is recovered and purified by known techniques. This process is illustrated as follows, where $R_1$ is defined as above:

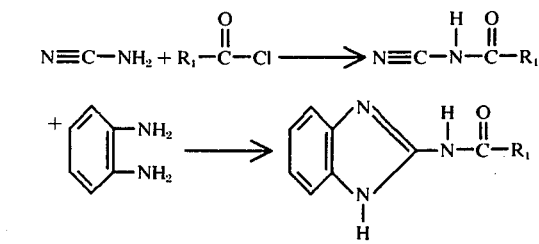

where $R_1$ and substituents on the benzene ring of the imidazole are as previously defined.

This process is particularly useful when substituents are present in the benzene ring. The large variety of substituted-o-phenylenediamines which are known in the art affords useful starting materials for this process.

Additional substituents can be introduced after formation of the 2-aroylamino and 2-heteroaroylaminobenzimidazole. Reaction of the $N^1$-nitrogen in the benzimidazole moiety with alkylating and acylating agents takes place readily. Substitution in the ring systems by conventional reactions such as nitration, halogenation, sulfonation and the like may also be accomplished using known procedures.

Different substrates require varied UV-absorber solubility properties for compatibility. A distinct advantage of the above defined 2-aminobenzimidazoles lies in the wide variety of compounds which can be made. For example one skilled in the art can readily prepare effective compounds containing the key grouping as outlined above to obtain the necessary UV absorption, along with highly-branched alkyl or carboxyl groups, the former to provide oil solubility and the latter, to provide aqueous solubility. Even strongly acid substituents such as sulfonic acid groups can be made part of the molecule by the conventional sulfonation procedures. These can be introduced at the outset of a synthetic scheme; for example, the known o-phenylenediamine substituted with a sulfonic acid grouping in the 3-, 4-, or 5-position can be converted to 2-aminobenzimidazoles containing the corresponding sulfonic acid group by known procedures. Subsequent reaction with aroyl and heteroaroyl halides following the above procedures gives sulfonated 2-aminobenzimidazoles which are water soluble at neutral or slightly alkaline pH. They can be made oil soluble by reaction with organic aminos. Metal salts of these compounds can be synthesized. For example, the magnesium salt of N-(5-sulfobenzimidazol-2-yl)-4-chlorobenzamide is readily prepared by treating with magnesium carbonate, to give a salt which can be incorporated in a UV-sensitive plastisol.

The general synthetic procedures outlined above are applicable for the preparation of the compounds utilized in this invention. However, when there are other substituents present containing active hydrogen such as hydroxyl, amino or mercapto, for example, blocking techniques may be needed to prevent acylation of these groups. These techniques are well known to those skilled in the art and comprise such reactions as the protection of the hydroxyl or mercapto by esterification, benzylation of the amine, or prior acylation. If desired, after reaction of the aroyl or heteroaroyl halide or anhydride with 2-amino-group in the benzimidazole, the blocking groups may be removed from the other substituent. Benzyl groups can be removed from the benzylated hydroxyl, amino or mercapto substituent by reduction with sodium in liquid ammonia, or catalytically with platinum and hydrogen. Corresponding acyl derivatives derived from lower aliphatic acids are more readily hydrolyzable than the 2-aroylamino or heteroaroylamino groups and can be selectively saponified. These and other techniques, well known in the art, can be utilized.

Relatively strong acids are required to form salts with the 2-aroylamino and the 2-heteroaroylaminobenzimidazoles. Mineral acids such as hydrochloric, nitric, sulfuric, and phosphoric acids can be used, as well as organic acids with sufficient acidity. These include, for example, citric acid, salicylic acid, phthalic acid and lactic acids, either as dilute solutions or at very high concentrations. Quaternary ammonium salts can be made with methyl iodide, benzyl chloride, methyl p-toluenesulfonate and the like. The alkaline salts can be prepared from inorganic bases or organic bases. Other salt-forming groups may be present as substituents on the benzene ring of the benzimidazole; these include amino, alkyl-, aralkyl-, and aryl-substituted- amino, or carboxyl. Similar substitution may be present on the aroyl and heteroaroyl radicals at $R_1$. When the aroyl moiety is substituted with a second aroyl group, for example, N-(benzimidazol-2-yl)-2-benzoylbenzamide, various derivatives of the ketonic group can be utilized such as the oxime, the phenylhydrazone, semicarbazone, etc. The carbonyl of the benzoyl group comprising the ketonic portion can be hydrogenated to the alcohol, that is, a benzhydrol derivative prepared, or the carbonyl can be condensed with a second mole of 2-aminobenzimidazole or other amines.

The processes for synthesizing the N-(benzimidazol-2-yl)-phthalimides and the N,N'-bis(benzimidazol-2-yl)-phthalamides, isophthalamides and terephthalamides, as well as the N-(benzimidazol-2-yl)alkoxycarbonylbenzamides derived therefrom are shown in Flow Sheet I.

Benzene polycarboxylic acid chlorides or anhydrides such as phthalic anhydride or isophthalic acid, terephthalic acid or anhydro trimellitic acid chloride react with 2-aminobenzimidazole to form N-(benzimidazol-2-yl)phthalimide derivatives when there are two carboxy groups in ortho position in the benzene ring, and N,N'-bis(benzimidazol-2-yl)phthalamide derivatives when there are two carboxy groups in the meta or para positions. (Compare compounds II, V, VIII and XI of Flow Sheet I). All of these compounds are excellent UV absorbers.

The phthalimide ring then can be opened by heating with an alkanol so as to form the corresponding N-(benzimidazol-2-yl)-2-(alkoxycarbonyl)benzamide (Compounds III, XIIA and XIIB). The N-(benzimidazol-2-yl)-3(or 4)-(alkoxy-carbonyl)-benzamides are prepared preferably, by first converting the isophthalic acid or terephthalic acid to the alkoxycarbonyl benzoyl chloride, followed by reaction of the latter compound with 2-aminobenzimidazole. (Compare compounds VI, IX, XIIA and XIIB). The latter compounds likewise show excellent properties as UV absorbers. Selective hydrolysis of the ester compounds (III, VI, IX, XIIA and XIIB) with alkali forms the salts of N-(benzimidazol-2-yl)carboxybenzamide. Acidification with dilute mineral acid to pH 3 yields the free carboxylic acid derivatives. Amine salts can then be prepared by reacting the carboxylic acid with a slight stoichiometric excess of primary, secondary or tertiary amines such as methylamine, ethylamine, diethylamine, triethylamine, and the like.

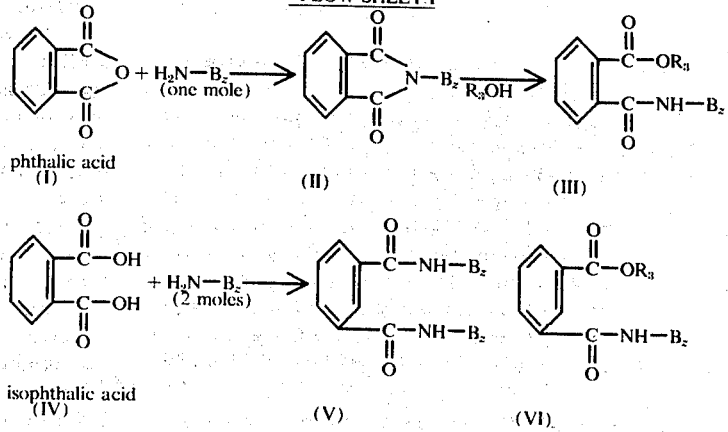

FLOW SHEET I

-continued
FLOW SHEET I

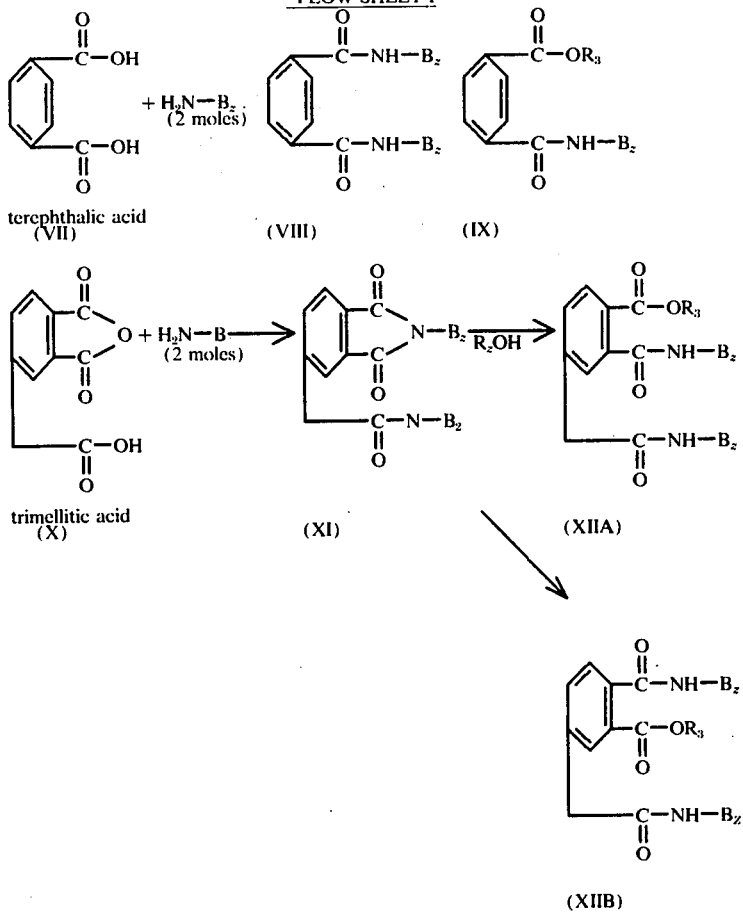

$R_3$ = alkyl
$B_z$ = a(benzimidazol-2-yl) group
The benzene ring of the benzimidazol or phthalic acid compound may be unsubstituted, or substituted by one of the groups listed on page 3.

More detailed information as to these processes is set forth in the examples.

The benzene ring of the benzene polycarboxylic acid compounds and/or the 2-aminobenzimidazole used as starting materials can be further substituted by groups such as alkyl, alkoxy, halo, phenyl, and the like as defined on page 3.

The wide selection of compounds which can be made by the process of this invention enables one to obtain a product with the desired physical properties and compatibility for a particular resin or for other use while at the same time maintaining the remarkable UV absorption characteristics of the N-(benzimidazol-2-yl)benzamides. The N-(benzimidazol-2-yl)-derivatives of phthalimide, isophthalamide and terephthalamide have excellent compatibility, especially with the plastic materials made from the corresponding phthalic acid, for example, with the alkyd, Mylar, and Terylene resins (see THE MERCK INDEX OF CHEMICALS AND DRUGS, Seventh Edition, 1960, MERCK & CO., Inc., Rahway, New Jersey, pages 698–699 and 1018, respectively).

The N-(benzimidazole-2-yl)phthalimides and phthalamides are also compatible with various plasticizers which are widely used in the plastics industry, including compounds such as n-heptylphthalate, di-2-ethyl-hexylphthalate, butylnonylphthalate, or butylbenzylphthalate.

The efficiency of candidate chemicals as UV abers has been studied in a variety of systems. Although accelerated tests are only indicators of potentially useful products, they serve to eliminate those compounds which themselves degrade on such exposure. One technique used involves the incorporation of the candidate chemical in a specific resin system to produce a transparent film when cast on glass. The film is removed from the glass, stored for one week at ambient room temperature in the dark and then randomly distributed 20 inches beneath a bank of three Westinghouse RS sunlamps, 275 watts, for exposures. The equipment is mounted in a hood through which a flow of air is maintained across the films. A "Colormaster" differential colorimeter is used to measure colors; a white porcelain enamel color plate is used as the standard. For plates, using a Bird film applicator. The plates are then stored in the cabinet with ventilation, but protected from light, and the films allowed to cure for one week at ambient temperature and humidity. Approximately ½ mil films result. The exposure then to the UV-light is run for varying periods of time. Within one week, using varying levels of UV-light absorber, it is possible to distinguish between compounds which are capable of protecting the polymer system from extreme yellowing and those which fail. Comparisons are made, for example, between 2-(o-hydroxyphenyl)benzotriazole and the 2-amido-benzimidazoles. Under these conditions of test, 2-amido-benzimidazole compounds show similar protective capabilities without the inherent drawbacks which characterize the hydroxyphenyl-substituted benzoheterocyclic derivatives.

The UV absorbing compounds of the present invention are used for the control of deterioration of a UV sensitive substance by ultraviolet light. There are several fields of application, for example:

1. The UV absorber may be incorporated in an ultraviolet sensitive composition especially a plastic, to protect it from discoloration, impairment of tensile strength, embrittlement or other deleterious reactions caused by ultraviolet rays. The UV absorber may be incorporated in the plastic composition before, during, or subsequent to the manufacture of the latter by way of a suitable operation.

2. The UV absorber may be incorporated in a composition to protect an ingredient thereof, for example, a dye, plasticizer or antimicrobial agent from attack by ultraviolet light.

3. The UV absorber may be incorporated into a composition to protect an underlying substratum to which the composition is to be applied from the attack of ultraviolet rays, e.g. use in suntan lotions or creams to protect the skin.

In a preferred embodiment of this invention, a plastic material is stabilized against deterioration caused by ultraviolet light, by having incorporated therein an effective amount of a 2-aryl (or heteroaryl) carboxamidobenzimidazole as a UV absorber. The plastic material to which the UV absorber is added may be in any conventional form such as a sheet, film, coating or fiber.

Practically all plastics undergo degration by prolonged exposure to UV radiation, especially in the region of 300–350 millimicrons. The deleterious results may result in objectionable yellowing of the plastic, cracks, diminished mechanical strength properties, and the like. Table II indicates the areas of sensitivity to UV of several common plastics.

Table II

| Synthetic Plastics | Wavelength (mμ) of Maximum Sensitivity |
|---|---|
| Polyethylene | 300 |
| Polypropylene (non-heat stabilized) | 310 |
| Polyvinyl chloride | 310 |
| Polystyrene | 318 |
| Polyvinyl chloride - copolymer with vinyl acetate | 322 and 364 |
| Polyesters (various formulations) | 325 |

Examples of plastic substrates include olefine polymers, polystyrene, cellulose esters, cellulose ethers, rubber, including various synthetic varieties, and vinyl resins derived from monomers such as vinyl chloride, vinyl acetate, vinylidene chloride, etc. Vinyl type resins include also copolymers of vinyl chloride with acrylonitrile, methacrylonitrile, vinylidene chloride, alkyl acrylates, alkyl methacrylates, alkyl maleates, alkyl furmarates, etc. Other UV sensitive plastics used commercially on a large scale in textile fibers include Nylon (polyamide), Perlon L (polyamide), Dacron (terephthalic acid and ethylene glycol), Orlon (polyacrylonitrile), Dynel (copolymer of acrylonitrile and vinyl chloride), Acrilan (polyacrylonitrile modified with vinyl acetate) [see MERCK INDEX, Seventh Edition, 1960, pages 740, 786, 1018, 757, 395 and 17 respectively] Saran (copolymer of vinylidine chloride and vinyl chloride), [see HACKH'S CHEMICAL DICTIONARY, Third Edition, 1944, McGraw-Hill Book Company, Incorporated, New York, New York], and the like.

The UV absorbing compounds of this invention are incorporated in plastic films by methods known in the art. Heat-stabilized polyvinyl chloride films are protected very simply by the addition of the 2-amido-benzimidazole prior to extrusion of the film. In a conical-shaped dry-powder blender, 98 parts of a copolymer of 75 parts vinylidene chloride and 25 parts vinyl chloride are mixed with 2 parts on N-(5-chlorobenzimidazol-2-yl)benzamide and extruded to produce a clear film. This film completely blocks out the deleterious energy. When UV-light-sensitive paper is placed under such treated film, no discoloration is produced. In comparison, untreated polyvinyl chloride film permits sufficient UV-light energy transmission to cause a severe yellowing. Similarly, when 5 parts of N-(5,6-dimethylbenzimidazole-2-yl)benzamide is dry-blended with a polystyrene powder, obtained from commercial sources, and the mixture formed into sheets by extrusion in the usual way, UV-light screening films are thereby obtained.

Polyvinyl chloride plastic compositions stabilized against ultraviolet light by the UV absorbers of this invention are used in the form of sheeting for automotive upholstery, as films for shower curtains, as extrusions for window blinds, and as a plastisol for casting or coating.

A typical formulation for the extrusion of window blinds is as follows: polyvinyl chloride, 100 parts; phthalate ester of long-chain aliphatic acid, 67 parts; tricresyl phosphate, 5 parts; polymeric resin, 5 parts; stabilizer/lubricant, ½ part; titanium dioxide, 4 parts; calcium carbonate, 25 parts; and stearic acid, 0.25 part. To this resin mix is added the UV-stabilizer, such as 2-benzamidobenzimidazole, at a general level of 1.75 parts. The ingredients are dry-blended and then extruded at fusion temperatures. Without the presence of an effective UV-absorber, the effects of UV-degradation would be to cause discoloration, brittlement and, finally, serious loss of mechanical strength. Similarly, sheeting and film must have UV-absorber addition when use-conditions cause exposure to such radiation. Calcium carbonate is an essential part of all polyvinyl formulations and calcium carbonate can cause discolorations with the hydroxyphenyl-substituted UV-absorbers of the prior art. It is an advantage of the present invention that any hydrogen chloride which may be generated from the breakdown of polyvinyl chloride would have no adverse effects upon the 2-amidobenzimidazoles.

Vinyl sheeting is also used as a surfacing agent over plastic panels which form a part of illumination ceiling structures. Indoors, fluorescent lights are emitters of sufficient UV-light to cause premature aging and discoloring of plastics. Incorporation of the UV-absorber in the resin or in the film serves to minimize this damage.

Cellulose films are made, for example, using 270 parts by weight of alkali cellulose derived from 77 parts of cellulose, 24.3 parts of carbon disulfide and 17.5 parts of sodium hydroxide. The carbon disulfide is added in one portion and the mixture is agitated in a suitable dough mixer at about 20° C. for 22 hours. After xanthation is complete, the resulting mixture is diluted with 595 parts of water. At this stage, the 2-substituted-amidobenzimidazole is added and mixed until dissolved or completely dispersed. Resultant solutions are then aged at ca. 5° C. Next, vacuum is applied to remove air bubbles from the solution, and the material is regenerated in film form in the usual manner by extrusion through a slit into an aqueous bath containing 10% sulfuric acid, 1% zinc sulfate, 14% sodium sulfate, 10% glucose and the balance, water.

The compounds of this invention are also added to a moisture-proof coating (lacquer) of the regenerated cellulose film as well as to the substrate. Solutions of the 2-amidobenzimidazoles can be added to the lacquer solution so that upon solvent evaporation a residual concentration of 1–5% of the 2-amidobenzimidazole is contained in the lacquer film. Removal of the solvent by warm air drying does not volatilize nor discolor the compounds. When used in such concentrations as indicated, there is complete blocking of UV-light transmission from a range of 290–390 millimicrons. When clarity of the film is of utmost importance to its end-use, it is preferable to employ the more soluble 2-amidobenzimidazoles, for example, N-(benzimidazol-2-yl)-4-carboethoxybenzamide or N-(benzimidazol-2-yl)-4-methoxybenzamide.

Polyethylene is used to coat many substrates in a technique which consists of dusting on finely-powdered polyethylene to a moving belt of the material to be covered, for example, textiles, tarpaulins, or even metals. The substrate containing a layer of finely-divided polyethylene on the surface speeds through a heating tunnel or oven which is maintained just above the fusion temperature of the polyethylene, so that a thin liquid layer forms. From the oven the material passes through a nip roll and chill roll combination for both thoroughly spreading the liquid film over the entire surface and then causing solidification. The polyethylene coating thereby achieved needs protection against UV-degradation. In those applications where opaque materials cannot be tolerated, this can be readily accomplished by pre-mixing in ribbon or conical powder blenders from 0.2–2% of N-(benzimidazol-2-yl)-4-t-butylbenzamide. The 2-amidobenzimidazole is finely divided to the same particle range as the polyethylene, prior to mixing. The mix is then fed from the hopper to the moving belt formed by the substrate. The compounds of this invention are suitable for such application because of their non-volatility and heat stability, along with compatibility with the resin system, especially in the molten state.

Clear gloss exterior finishes are used as top coats over wood, masonry, metal and other substrates to provide a durable coating. In typical formulation, the clear finish is prepared from two parts. One component is the clear base which is made by dissolving 278 lbs. of an oxirane-modified ester resin in 100 lbs. of a light petrolum solvent and 28.7 lbs. of ethylene glycol ethyl ester acetate. The second component is the clear activator. It consists of 417 lbs. of polyester solution, 50 lbs. of 15% cellulose acetate butyrate solution and 29.6 lbs. of ethylene glycol ethyl ether acetate to which is added 115 lbs. of N-(benzimidazol-2-yl)-4-methoxybenzamide. The clear finish is made by mixing 406.7 parts of part one clear base with 511.6 parts of the clear activator (part two). The UV-absorber concentration, based on resin solids, is about 3.0% by weight.

Nylon-type resins are used in the manufacture of fibers for carpeting, hoisery, garments and the like. The resins are melted in an inert atmosphere and at temperatures of 230°–275° C., and then extruded through spinnerets. The melting of the resin is done in a batch operation; heat exposure is of such duration that only the most stable additives can be employed successfully by addition to the resin melt. The 2-amidobenzimidazoles are extremely stable to elevated temperatures and can be incorporated in the melt at levels from 0.2–5% prior to extrusion. The need for UV protection in the resin systems is especially apparent when other additives such as antimicrobial agents or dyes are also present. N,N'-bis(benzimidazol-2-yl)terephthalamide is unaffected by temperatures up to 340° C. Other resin systems for which this agent finds particular utility are the polyesters derived from terephthalic acid and polyethylene glycols.

These, too, are used as fibers for textile application as well as carpeting and the like. For this purpose the 2-amidobenzimidazoles are finely powdered and then blended with Nylon-6 powder at room temperature in the ratio of 0.3 part of the benzimidazole to 99.7 parts Nylon. The powder is then heated gradually in a nitrogen atomsphere; at 225° C. melting begins and the mix finally becomes a water-white liquid. The melt could be brought to temperatures as high as 270° C. for spinning into fiber or for use in molding operations.

In another embodiment of this invention the UV absorber is incorporated in a composition to protect an ingredient thereof from attack by ultraviolet rays. Organomercurial salts, for example, phenylmercury acetate, propionate and oleate, are widely used to protect such vulnerable substrates as coatings and plastics from microbial deterioration. These mercurials are degraded rapidly upon exposure to ultraviolet radiation. They are used in concentrations of from about 0.05–0.5% by weight, especially in substrates which are for use outdoors. Transparent sheeting containing such antimicrobial agents must have UV absorbers incorporated to protect not only the plastic sheeting but also the microbial inhibitor from light deterioration. Usually from about 0.1 to about 0.5% by weight of a 2-carboxamidobenzimidazole, for example, will impart such a protective action.

Similarly, vinyl fabric used on outdoor furniture undergoes a shortened useful life unless not only the antimicrobial agent but also the plasticizers contained therein are protected against UV. It is known that dialkyl phthalate and other well known and commonly used esters cannot withstand absorption of UV energy without degradation.

In still another embodiment of this invention the UV absorber is employed for those uses where a composition is applied to a substrate that is normally subject to deterioration by ultraviolet light. For example, in comestibles, of which more or less temporary protection is desired, the material is enclosed with a transparent plastic wrapping containing the UV absorber which serves as a filter for the harmful rays. Another example of a use of this type is in lacquers, clear coatings and paints for wood and the like.

Suntan screening preparations commonly in use on human skin generally must perform satisfactorily for periods of less than 24 hours. Re-application of the formulation must be made on subsequent exposure days because of prior removal by washing or bathing. A stable and useful preparation consists of the following:

| Chemical | Parts By Weight |
| --- | --- |
| N-(benzimidazol-2-yl)-2-(n-butoxycarbonyl)benzamide | 0.5 |
| Polyethylene glycol, m.w. 300 | 42.5 |
| Propyleneglycol | 25.0 |
| Isopropyl myristate | 2.5 |
| Ethanolquinine | 29.2 |
| Perfume | 0.03 |

The formulation is applied either by lightly dabbing the skin or spraying.

The UV absorber may also be incorporated in a suntan formulation containing insect repellents, for example:

| Chemical | Parts By Weight |
| --- | --- |
| N-(benzimidazol-2-yl)-4-ethoxycarbonyl)benzamide | 0.5 |
| Adipic acid isopropyl-tetrahydrofurfuryl ester | 14.5 |
| Metatoluic acid diethylamide | 5.0 |
| Phthalic acid dimethyl ester | 8.0 |
| Ground-nut oil | 36.0 |
| Paraffin Oil | 36.0 |

The formulation can be applied by lightly rubbing into the skin for achieving both effects, that is screening of UV-light and the repelling of insects.

The N-(benzimidazol-2-yl)benzamides are also useful for protecting hair-setting and hair-grooming gels. These preparations can contain thickening or gelling agents which are amine salts of resin carboxylic acids. Some of the amines employed are di(2-ethylhexyl)amine and di(isopropanol)amine. Lanolin, fatty acid esters and ethoxylated lanolin are also components of the formulations. Generally, about 0.2% to 0.5% by weight of the UV absorber is required.

The following examples are given for the purpose of illustration and not by way of limitation.

EXAMPLE 1

N-(Benzimidazol-2-yl)-4-tert-butylbenzamide

A mixture of 18 g. of p-tert-butylbenzoic acid and 25 g. of thionyl chloride are refluxed for 1 hour. The thionyl chloride is stripped under reduced pressure, and to insure complete removal, two 50 ml. portions of benzene are added successively and stripped. The liquid residue is distilled under reduced pressure and the colorless liquid boiling at 100° C. at 2.2 mm. pressure is collected; yield 15.7 g.

2-Aminobenzimidazole (10.7 g.) is dissolved in 100 ml. of dry pyridine, mixed with 15.7 g of p-tert-butyl-benzoyl chloride and heated for 1 ½ hours on a steam bath. The mixture is cooled to room temperature and poured into 600 ml. of water; the precipitated product is removed by suction filtration, washed well with water and dried under vacuum at 60° C. The yield of crude product is 22.5 g. It is recrystallized from a small volume of glacial acetic acid containing 1 ml. of water for each 15 ml. of acid. Long colorless needles are thereby obtained, m.p. 246°–248° C., λmax. 302 mµ, $E_1^{1\%}{}_{cm.}$ 737.

In accordance with the above procedure, but using an equivalent quantity of p-methoxybenzoyl chloride, p-methylbenzoyl chloride or o-fluorobenzoyl chloride in place of p-tert-butylbenzoyl chloride there is obtained as a product N-(benzimidazol-2yl)-4-methoxybenzamide, N-(benzimidazol-2-yl)-4-methylbenzamide, or N-(benzimidazol-2-yl)-2-fluorobenzamide, respectively.

Following the above procedure, using as reactants benzoyl chloride and equivalent quantities of 2-amino-5-dodecyloxybenzimidazole, 2-amino-4-phenylbenzimidazole, 2-amino-1-(n-butyl)benzimidazole, 2-amino-1-phenylbenzimidazole, or 2-amino-1-(methoxycarbonyl)benzimidazole, there is obtained as a product, N-(5-dodecyloxybenzimidazol-2-yl)-4-benzamide, N-(4-phenylbenzimidasol-2-yl)-4-benzamide, N-(1-n-butyl) benzimidazol-2-yl)-4-benzamide, N-(1-phenyl)-benzimidazol-2-yl)-4-benzamide, or N-(1-methoxycarbonyl)benzimidazol-2-yl)-4-benzamide, respectively.

EXAMPLE 2

2-(Thiazole-4-carboxamido)benzimidazole

2-Aminobenzimidazole (6.7 g.) is dissolved in 50 ml. of pyridine and reacted with 8.0 g. of thiazole-4-carboxylic acid chloride by heating on a steam bath for 3 hours. The cooled reaction mixture is poured into 200 ml. of water, stirred for 1 hour and then suction filtered. The product is purified by solution in hot alcohol, filtration from a small amount of insolubles and gradual cooling. The compound melts at 294°–296° C., λmax. 303 mµ, $E_1^{1\%}{}_{cm.}$ 790.

Substitution of an equivalent amount of other heterocyclic acid chlorides, e.g., pyridine 2-, 3-, and 4-carboxylic acid chlorides; thenoyl 2- and 3-chlorides, coumariloyl chloride for thiazole-4-carboxylic acid chloride provides a convenient synthesis for: 2-(pyridine-2-carboxamido)benzimidazole, 2-(pyridine-3-carboxamido)benzimidazole, 2-(pyridine-4-carboxamido)benzimidazole, 2-(thiophene-2-carboxamido)-benzimidazole, 2-(coumariloyl)aminobenzimidazole, m.p. 293°–295° C. λmax. 327 mµ, $E_1^{1\%}{}_{cm.}$ 1024 and 2-nicotinamidoaminobenzimidazole, λmax. 319 mµ, $E_{1cm.}^{1\%}$ 429.

EXAMPLE 3

2-(2'-Thenoyl)aminobenzimidazole

A suspension of 5.56 g. (0.02 mole) of 2-methylthiopseudourea sulfate, 4.0 g. (0.04 mole) triethylamine and 50 ml. of dimethylformamide is cooled to 0° C. and treated with a solution of 5.88 g. (0.04 mole) of 2-thenoyl chloride in 15 ml. of dimethylformamide. The reaction mixture is allowed to warm to room temperature, stirred for 2 hours and is then poured onto 500 g. of an ice-water mixture. The colorless solid product is separated by filtration and washed with water. This solid is recrystallized from ethanol to give 1,3-dithenoyl-2-methylthio-pseudourea, m.p. 166°–167° C.

A solution of 1.55 g. (0.01 mole) of 1,3-dithenoyl-2-methylthio-pseudourea and 1.08 g. of o-phenylenediamine in 50 ml. of ethanol is refluxed for 5 hours. The solid is then removed in vacuo and the residue is recrystallized from ethanol. The yield is substantially pure 2-(2'-thenoyl)aminobenzimidazole, m.p. 303°–305° C.

When thiazole-4-carbonyl chloride or picolinyl chloride is employed in the above process in place of thenoyl chloride, there is obtained 2-(4'-thiazolylcarbonyl)aminobenzimidazole or 2-(2'-picolinoyl-)aminobenzimidazole, respectively.

EXAMPLE 4

4-Methyl-2-benzoylaminobenzimidazole

Cyanamide (3.44 g.) is dissolved in 69 ml. of pyridine and the mixture is held at 0°–4° C. While stirring, benzoyl chloride (11.5 g.) is added in portions. The reaction mixture is maintained at 0°–4° C. for 15 minutes. 3-Methyl-o-phenylenediamine (10 g.) is then added to the reaction mixture, and the resulting product is kept at room temperature for a few hours and then heated on a steam-bath for about 2.5 hours. After cooling to room temperature, the mixture is evaporated under reduced pressure, poured into 200 ml. water, and rubbed until solid. The product is removed by suction-filtration, dissolved in 5% aqueous sodium hydroxide solution, and clarified by gravity filtration. The benzimidazole derivative is precipitated by the addition of the alkaline solution to a slight excess of dilute acetic acid.

EXAMPLE 5

5-Chloro-2-(2'-furoyl)aminobenzimidazole

5-Chloro-2-aminobenzimidazole (5.0 g., 0.03 mole) and 2-furoyl chloride (3.9 g., 0.03 mole) is mixed in 25 ml. of pyridine and heated for 2 hours on the steam bath. It is then cooled to room temperature, poured into 250 ml. of water, mixed ½ hour and then suction filtered. A yield of 7.3 g. is obtained. The product is purified by recrystallization from a 75% aqueous solution of acetic acid. On drying at 80° C. and 1 mm. pressure for 12 hours, it is obtained as an acetic acid solvate, m.p. 249°–251° C., corresponding to the empirical formula $C_{12}H_8N_3O_2Cl.CH_3COOH$. On further drying the sample at 130° C. and 1 mm. for 4 hours, the acetic acid is removed, m.p. 250°–251° C., λmax. 310 mμ, $E_1^{1\%}{}_{cm.}$ 938.

Similarly 2-(2-furanacrylyl)aminobenzimidazole, m.p. 250°–251° C., λmax. 329 mμ, $E_1^{1\%}{}_{cm.}$ 1477 is obtained by reaction of an equivalent quantity of 2-furanacrylic acid with 2-aminobenzimidazole.

EXAMPLE 6

2-(5'-tert-butyl-2'-furoyl)aminobenzimidazole

5-Tert-butyl-2-furoic acid chloride is prepared from the corresponding furoic acid and thionyl chloride according to the method of H. Gilman and N. O. Calloway, J. Am. Chem. Soc., 55, 4197–4205 (1933). 7.1 G. of 5-tert-butyl-2-furoyl chloride and 5.1 g. of 2-aminobenzimidazole are reacted in 35 ml. of pyridine by heating on a steam bath for 2 hours. The reaction mixture is cooled to room temperature and poured into 250 ml. of water, stirred 15 minutes and then suction filtered. A yield of 10.9 g. is obtained. The product is recrystallized from acetic acid containing 30% of water. Long colorless needles are obtained, as an acetic acid solvate, which melts at 257°–258° C. A sample dried at 80° C. at 1 mm. pressure for 16 hours still retained the acetic acid. It is then dried for 4 hours at 130° C. at 0.1 mm. for removal of the acetic acid. The compound then melts at 257.5°–259° C., λmax. 312 mμ, $E_1^{1\%}{}_{cm.}$ 956.

In accordance with the above procedure but starting with the appropriately substituted 2-furoyl chloride, the following products are obtained: 2-(5'-phenyl-2'-furoyl)aminobenzimidazole, m.p. 247°–248.5° C., λmax. 334 mμ, $E_1^{1\%}{}_{cm.}$ 1245 and 2-(5'-benzoyl-2'-furoyl) aminobenzimidazole, m.p. 269°–271° C., λmax. 345 mμ, $E_1^{1\%}{}_{cm.}$ 785.

EXAMPLE 7

N-(Benzimidazol-2-yl)-2-(n-butoxycarbonyl)benzamide (III)

2-Aminobenzimidazole (13.3 g.) is dissolved in 50 ml. of pyridine, and 10.2 g. of phthaloyl chloride is added, causing immediate precipitation. On mixing and heating on the steam-bath, all dissolves. The solution is heated 2 hours on the steam-bath with occasional swirling. It is cooled to room temperature and quenched in 200 ml. of water. After 1 hour agitation, the mixture is filtered free of solids and the solids washed with water. The yield of N-(benzimidazol-2-yl)phthalimide is 11.6 g. Recrystallization from glacial acetic acid results in bright yellow crystals of N-(benzimidazol-2-yl)phthalimide which, after drying, melts at 266°–268° C., λmax. 295.0, $E_1^{1\%}{}_{cm.}$ 529.

N-(Benzimidazol-2-yl)phthalimide (4 g.) in 200 ml. of n-butyl alcohol is heated at 115° C. for 35 minutes. On cooling, colorless needles form. These are removed by suction filtration, washed with butyl alcohol and finally with diethyl ether. After drying for three hours at 125° C. under vacuum, a yield of 2.5 g. of N-(benzimidazol-2-yl)-2-(n-butoxycarbonyl)-benzamide, m.p. 187° C., is obtained. Additional heating to higher temperatures causes a reclosure to the phthalimide and remelting which corresponds to the phthalimide, m.p. 267°–268° C.

Other esters such as the methyl, propyl, and higher alkyl derivatives are prepared from the N-(benzimidazol-2-yl)phthalimide using methanol, propanol, or higher alkanols in place of butyl alcohol. In this manner, the following compounds are prepared: N-(benzimidazol-2-yl)-2-methoxycarbonylbenzamide, N-(benzimidazol-2-yl)-2-isopropoxycarbonylbenzamide, and N-(benzimidazol-2-yl)-2-dodecyloxycarbonylbenzamide.

Replacement of 2-aminobenzimidazole in the first step with an equivalent weight of ring-substituted 2-aminobenzimidazole, followed by reaction with the phthaloyl chloride, gives N-(substituted-benzimidazol-2-yl)phthalimide. This compound is then converted to the corresponding (2-alkoxycarbonyl)benzamide by the procedures outlined. The following compounds are prepared according to this method: N-(5-chlorobenzimidazol-2-yl)-(2-methoxycarbonyl)benzamide using 5-chloro-2-aminobenzimidazole in Step 1 and methanol in Step 2; N-(5,6-dimethylbenzimidazol-2-yl)-(2-n-butoxycarbonyl)benzamide from 5,6-dimethyl-2-aminobenzimidazole in Step 1 and n-butanol in Step 2; N-(5-acetamidobenzimidazol-2-yl)-(2-n-isopropoxycarbonyl) benzamide from 5-acetamido-2-aminobenzimidazole in Step 1 and isopropanol in Step 2; N-(1-butylbenzimidazol-2-yl)-(2-methoxycarbonyl)benzamide from 1-butyl-2-aminobenzamidazole in Step 1 and methanol in Step 2.

Similarly, replacement of phthaloyl chloride with an equivalent weight of substituted phthaloyl chloride, followed by reaction with 2-aminobenzimidazole, forms the corresponding phthalimides in Step 1. These are reacted as described in Step 2 with alcohols to form the corresponding substituted (2-alkoxylcarbonyl)benzamides. Typical compounds prepared by this method are: N-(benzimidazol-2-yl)-(2-methoxycarbonyl)-5-phenylbenzamide, N-(4-methylbenzimidazol-2-yl)-(2-n-butoxycarbonyl)-3-chlorobenzamide and N-(5-dodecyloxybenzimidazol-2-yl)-(2-ethoxycarbonyl)-4-t-butylbenzamide.

EXAMPLE 8

N,N'-bis(benzimidazol-2-yl)-isophthalamide (V)

2-Aminobenzimidazol (13.3 g.) is dissolved in 50 ml. of pyridine and reacted with 10.2 g. of isophthaloyl chloride. Complete solution is obtained initially and after 1 ½ hours of heating on the steam bath abundant solids are evident. The mixture is cooled to room temperature and dumped into 250 ml. of water. After one hour of agitation, the product is removed by suction filtration. It is purified by recrystallization from glacial acetic acid. The yield of crude product is 14.6 g. The purified compound does not melt at temperatures up to 320° C. and there are no visible signs of decomposition during this heating. The product shows λmax. 319, $E_1^{1\%}{}_{cm.}$ 950.

Replacement of 2-aminobenzimidazole with an equivalent amount of 5,6-dimethylbenzimidazole followed by reaction with isophthaloyl chloride gives N,N'-bis(5,6-dimethylbenzimidazole-2yl)isophthalamide.

EXAMPLE 9

N,N'-bis-(benzimidazol-2-yl)terephthalamide (VIII)

2-Aminobenzimidazole (13.3 g.) and 10.2 g. of terephthaloyl chloride in 50 ml. of pyridine is heated on a steam bath for a total of 4 hours. In the first 15 minutes of reaction an additional 25 ml. of pyridine is added. The mixture is cooled to room temperature and poured into 300 ml. of water, mixed 1 hour and the product removed by suction filtration. The product is purified by recrystallization from dimethylformamide to which a small volume of water is added. The compound melts above 340° C., λmax. 334, $E_1^{1\%}{}_{cm.}$ 871.

Replacement of 2-aminobenzimidazole with an equivalent amount of 5-chlorobenzimidazole, followed by reaction with terephthaloyl chloride gives N,N'-bis(5-chlorobenzimidazol-2-yl)terephthalamide.

EXAMPLE 10

N-(Benzimidazol-2-yl)-4-(ethoxycarbonyl)benzamide (IX)

p-Ethoxycarbonylbenzoyl chloride is prepared according to the method of M. J. Dewar and J. P. Schroeder, J. Org. Chem., 30, 2297 (1965), by the gradual addition of a small amount of ethyl alcohol to a boiling solution of terephthaloyl chloride in benzene. After removal of the solvent the residue is distilled under reduced pressure to give the acyl chloride which boils at 102°–105° C. at 0.4 mm.

2-Aminobenzimidazole (9.8 g.) is dissolved in 100 ml. of pyridine and reacted with 16.3 g. of p-ethoxycarbonyl chloride by heating on a steam bath for 3 hours. The cooled mixture is poured into 600 ml. of water, agitated 1 hour and the product removed by suction filtration. It is then washed well with water and dried. A yield of 20.7 g. is obtained. It is purified by recrystallization from ethyl alcohol to give colorless needles, m.p. 224°–225.5° C., λmax. 322.5, $E_1^{1\%}{}_{cm.}$ 613.

Selective hydrolysis of the ester with 5–10% aqueous sodium hydroxide solution forms N-(benzimidazol2-yl)-4-carboxybenzamide, sodium salt. Acidification with dilute mineral acid to pH 3 yields the 4-carboxylic acid derivative. Amine salts can then be prepared by reacting the carboxylic acid derivative with a slight stoichiometric excess of primary, secondary or tertiary amine.

In accordance with the above procedures, but starting with the known p-methyl-, p-(n-propyl), p-(n-butyl), p-(n-amyl) or p-(n-decyl ester of benzoyl chloride, the corresponding N-benzimidazol-2-yl)-4-(alkoxycarbonyl)benzamide is obtained.

EXAMPLE 11

N-(Benzimidazol-2-yl)-4-(benzimidazol-2-yl-carbonyl)-phthalimide (XI)

Anhydrotrimellitic acid chloride (11 g.) is mixed with 13.3 g. of 2-aminobenzimidazole in 75 ml. of pyridine. A clear solution results on heating on the steam bath; after 3 hours, the reaction contains appreciable solids. The mixture is cooled to room temperature, poured into 400 ml. of water, agitated ½ hour and the product removed by suction filtration. A yield of 16.6 g. is thereby obtained. The product is purified by recrystallization from dimethylformamide. It is dried at 130° C. at 0.1 mm. pressure, m.p. 352°–353° C. Elemental analysis agrees with respect to carbon, hydrogen, and nitrogen for the formula $C_{23}H_{14}N_6O_3$ of a compound having the structure XI of Flow Sheet I.

The above phthalimido compound is heated with n-butyl alcohol following the procedure of the second step of Example 10 to open up the phthalimido linkage and give the corresponding n-butoxy compound, which is N,N'-bis(benzimidazol-2-yl)-3 or (4)-(n-butoxycarbonyl)-1,4(3)-phthalamide (Compound XIIA or XIIB).

Any departure from the above description which conforms to the present invention is intended to be included within the scope of the claims.

What is claimed is:

1. A N-(benzimidazol-2-yl)arylcarboxamide having the formula:

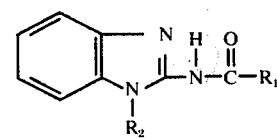

wherein $R_1$ is a phenyl group substituted at the 2-, 3- or 4-position by a member selected from the group consisting of methoxycarbonyl, ethoxycarbonyl, butoxycarbonyl, propoxycarbonyl, dodecyloxycarbonyl, carboxy, phenyl, nitro, and carboxamide and $R_2$ is a member selected from the group consisting of hydrogen, methyl, acetyl, methoxycarbonyl, butyryl, pivaloyl, stearoyl, acryl, toluyl, mesitoyl, butyl, octyl, benzoyl, halobenzoyl, and phenyl.

* * * * *